(12) United States Patent
Strumolo et al.

(10) Patent No.: US 6,470,278 B1
(45) Date of Patent: Oct. 22, 2002

(54) CONFINED OCCUPANT DETECTION APPARATUS AND TRANSPORTATION VEHICLE HAVING SAME INCORPORATED THEREIN

(75) Inventors: Gary Steven Strumolo, Beverly Hills, MI (US); Margherita Zanini-Fisher, Bloomfield Township, MI (US); Ronald Hugh Miller, Saline, MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 253 days.

(21) Appl. No.: 09/590,983

(22) Filed: Jun. 9, 2000

(51) Int. Cl.[7] ............................................. G01N 33/497
(52) U.S. Cl. .......................................... 702/24; 702/23
(58) Field of Search .......................... 73/861; 324/425; 356/437; 702/23, 24, 116

(56) References Cited

U.S. PATENT DOCUMENTS

| 5,745,030 A | 4/1998 | Aaron |
| 5,859,479 A | 1/1999 | David |
| 5,907,407 A | * 5/1999 | Atkinson et al. ........... 356/437 |
| 6,018,292 A | 1/2000 | Penny, Jr. |
| 6,024,388 A | 2/2000 | Tomah et al. |
| 6,067,167 A | * 5/2000 | Atkinson et al. ........... 356/437 |

* cited by examiner

*Primary Examiner*—Bryan Bui
*Assistant Examiner*—Douglas Washburn

(57) ABSTRACT

The present invention disclosed is an apparatus for detecting a confined occupant in a confined space in a transportation vehicle. A transportation vehicle contains an apparatus for detecting a confined occupant in a confined space in a transportation vehicle including a minimum of one carbon dioxide sensor, a method for detecting a confined occupant in a confined space in a transportation vehicle and a computing means having an algorithm for detecting a confined occupant in a confined space based upon analysis of a carbon dioxide concentration measured in a confined space of a transportation vehicle.

17 Claims, 2 Drawing Sheets

CONFINED OCCUPANT DETECTION APPARATUS AND TRANSPORTATION VEHICLE HAVING SAME INCORPORATED THEREIN

BACKGROUND OF THE INVENTION

1. Field of the Invention

The present invention relates generally to design and manufacturing of transportation vehicles. More particularly, the present invention relates to design and manufacturing of transportation vehicles having enhanced safety and security.

2. Description of the Related Art

In addition to designing and manufacturing transportation vehicles with an intent to provide transportation vehicles within enhanced levels of comfort, convenience, utility and economy, transportation vehicle manufacturers typically also endeavor to design and manufacture transportation vehicles which also provide a transportation vehicle owner, a transportation vehicle operator or a transportation vehicle occupant with an enhanced level of safety and an enhanced level of security.

While designing and manufacturing transportation vehicles with enhanced levels of comfort, convenience, utility and economy certainly presents to a transportation vehicle manufacturer competing and contradictory challenges which are often difficult to simultaneously satisfy or reconcile, designing and manufacturing transportation vehicles to provide a transportation vehicle owner, a transportation vehicle operator or a transportation vehicle occupant with an enhanced level of safety or an enhanced level of security often presents a unique challenge to a transportation vehicle manufacturer insofar as it is often not entirely clear to a transportation vehicle manufacturer, a transportation vehicle owner, a transportation vehicle operator or a transportation vehicle occupant the nature or extent of various types of transportation vehicle safety breaches and transportation vehicle security breaches which might present a diminished level of safety and a diminished level of security of a particular transportation vehicle with respect to a particular transportation vehicle owner, a particular transportation vehicle operator or a particular transportation vehicle occupant.

Nonetheless, notwithstanding an ambiguity with respect to the nature or extent of various types of transportation vehicle safety breaches and transportation vehicle security breaches which are plausibly of concern to a transportation vehicle owner, a transportation vehicle operator or a transportation vehicle occupant, it is generally recognized that being involuntarily confined, as a confined occupant, within a confined space within a transportation vehicle, such as but not limited to a confined trunk space within a passenger transportation vehicle, typically presents a safety breach (generally under circumstances where such confinement is accidental) or a security breach (generally under circumstances where such confinement is deliberate) to a transportation vehicle owner, a transportation vehicle operator or a transportation vehicle occupant.

It is thus towards the goal of providing, in general, transportation vehicles with enhanced levels of safety and security that the present invention is directed. It is similarly also towards the goal of providing, more particularly, transportation vehicles with enhanced levels of safety and security with respect to involuntary confinement of confined occupants within confined spaces within those transportation vehicles.

Various apparatus and methods have been disclosed in the art of transportation vehicle design, transportation vehicle development and transportation vehicle manufacturing for providing transportation vehicles with enhanced levels of safety and security, in particular with respect to involuntary confinement of confined occupants within confined spaces within transportation vehicles.

For example, Aaron, in U.S. Pat. No. 5,745,030, discloses an anti-carjacking system that employs multiple sensors and multiple enablement/disablement relays which in an aggregate provide a transportation vehicle within which an occupant is less likely to be involuntarily confined. Similarly, David, in U.S. Pat. No. 5,859,479, Penny, Jr., in U.S. Pat. No. 6,018,292 and Tomah et al., in U.S. Pat. No. 6,024,388, each disclose, at least in part, a trunk lock release mechanism which allows for release of a trunk lock latch by an occupant confined, either accidentally or deliberately, within a confined trunk space within a transportation vehicle, such as to provide for enhanced safety or enhanced security of the confined occupant with respect to the transportation vehicle.

Desirable in the art of transportation vehicle design, development and manufacturing are additional apparatus and methods that may be employed to provide transportation vehicles with enhanced safety and security, more particularly as directed towards apparatus and methods that may be employed to alleviate accidental or deliberate involuntary confinement of a confined occupant within a confined space within a transportation vehicle.

It is towards the foregoing object that the present invention is directed.

SUMMARY OF THE INVENTION

In accord with the object towards which the present invention is directed, there is provided by the present invention: (1) an apparatus for detecting a confined occupant within a confined space within a transportation vehicle; (2) the transportation vehicle having assembled therein the apparatus for detecting the confined occupant within the confined space within the transportation vehicle; and (3) a method for detecting the confined occupant within the confined space within the transportation vehicle.

In conjunction with each of the foregoing apparatus, transportation vehicle and method, there is employed: (1) a minimum of one carbon dioxide sensor; and (2) a computing means having programmed therein an algorithm appropriate for detecting a confined occupant within a confined space within a transportation vehicle based upon an analysis of a carbon dioxide concentration measured within the confined space within the transportation vehicle while employing the minimum of one carbon dioxide sensor. Similarly in conjunction with each of the foregoing apparatus, transportation vehicle and method, there may additionally be employed a means for opening the confined space within the transportation vehicle based upon detecting the confined occupant within the confined space, wherein the means for opening the confined space is effected by the computing means having programmed therein the algorithm.

BRIEF DESCRIPTION OF THE DRAWINGS

The objects, features and advantages of the present invention are understood within the context of the Description of the Preferred Embodiment, as set forth below. The Description of the Preferred Embodiment is understood within the context of the accompanying drawings, which form a material part of this disclosure, wherein.

DESCRIPTION OF THE PREFERRED EMBODIMENT

The present invention provides: (1) an apparatus for detecting a confined occupant within a confined space within a transportation vehicle; (2) the transportation vehicle having assembled therein the apparatus for detecting the confined occupant within the confined space within the transportation vehicle; and (3) a method for detecting the confined occupant within the confined space within the transportation vehicle. In general, in conjunction with each of the foregoing apparatus, transportation vehicle and method, there is employed: (1) a minimum of one carbon dioxide sensor; and (2) a computing means having programmed therein an algorithm appropriate for detecting a confined occupant within a confined space within a transportation vehicle based upon an analysis of a carbon dioxide concentration measured within the confined space within the transportation vehicle while employing the minimum of one carbon dioxide sensor.

The present invention may be employed for detecting a confined occupant within a confined space within a transportation vehicle including but not limited to a passenger transportation vehicle, a sport utility transportation vehicle, a light utility transportation vehicle and a heavy utility transportation vehicle. Similarly, typically and preferably, the confined space within the transportation vehicle within which is detected the confined occupant will be selected from the group including but not limited to a confined trunk space within a passenger transportation vehicle and a confined cargo space within a transportation vehicle other than a passenger transportation vehicle. Finally, the present invention may be employed for detecting within a confined space within a transportation vehicle a confined occupant selected from the group including but not limited to a confined adult human occupant, a confined juvenile human occupant, a confined infantile human occupant, and a confined carbon dioxide respiring animal occupant.

Figure 1:
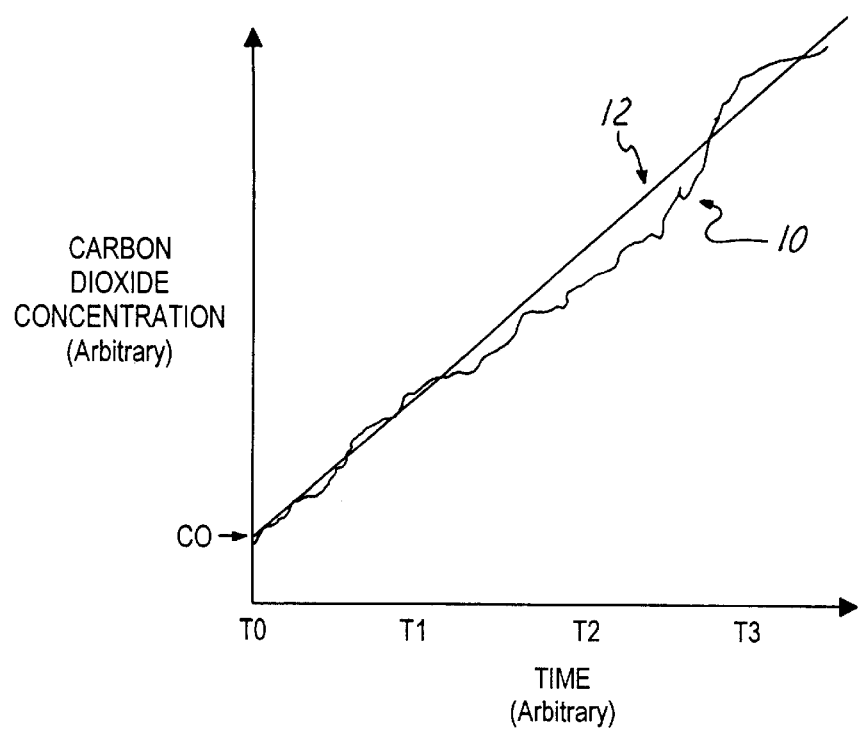
FIG. 1 shows a plot of Carbon Dioxide Concentration versus Time for a confined occupant within a confined space within a transportation vehicle.

Referring now to FIG. 1, there is shown a plot of Carbon Dioxide Concentration versus Time for a confined occupant within a confined space within a transportation vehicle in accord with the present invention.

As is illustrated within the plot of FIG. 1, the curve corresponding with reference numeral 10 corresponds with a series of measured data points for carbon dioxide concentration as a function of time and the line corresponding with reference numeral 12 corresponds with a linear least squares fit of the series of measured data points for carbon dioxide concentration as a function of time. Although within the plot of FIG. 1 both carbon dioxide concentration and time are expressed in terms of arbitrary units, for purposes of further defining the scope of the present invention, it is anticipated that a 20 kilogram juvenile human confined occupant within a confined space typically produces carbon dioxide at a rate of about 4E-5 moles per second, which in a confined space of about 37 cubic feet would provide a carbon dioxide concentration rise of about 1000 parts per million (ppm) over a period of 20 minutes (i.e. a rate of increase of about 50 ppm/min). Clearly, factors such as but not limited to confined space volume, confined space integrity and confined occupant metabolic rate may significantly influence within a confined space within a transportation vehicle a rate of rise of carbon dioxide attributed to a confined occupant within the confined space within the transportation vehicle, and thus such factors demand adequate consideration in accord with the present invention.

Figure 2:
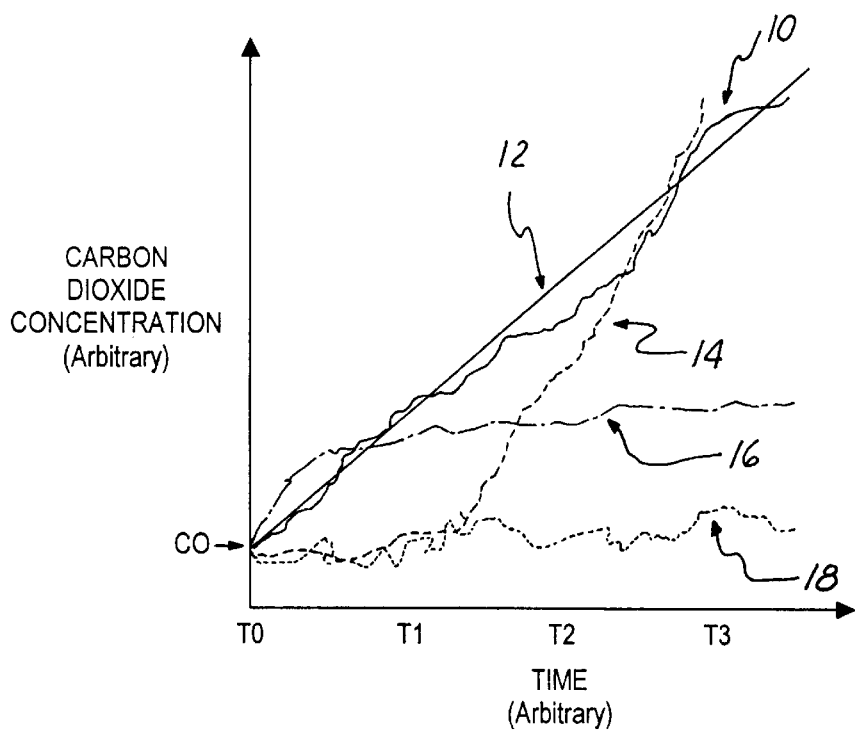
FIG. 2 shows a plot of Carbon Dioxide Concentration versus time for various sources of carbon dioxide within a confined space within a transportation vehicle.

Referring now to FIG. 2 there is shown a plot of Carbon Dioxide Concentration versus Time for various sources of carbon dioxide within a confined space within a transportation vehicle.

Shown in FIG. 2 is a plot generally analogous with the plot of FIG. 2 and wherein the curve which corresponds with reference numeral 10 and the line which corresponds with reference numeral 12 are equivalent with the curve which corresponds with reference numeral 10 and the line which corresponds with reference numeral 12 as shown within FIG. 1, but wherein there are shown three additional curves, one each corresponding with reference numeral 14, reference numeral 16 and reference numeral 18.

The curve that corresponds with reference numeral 14 is intended to represent a carbon dioxide concentration profile for a confined occupant within the confined space within the transportation vehicle, but wherein the confined occupant is confined within the confined space within the transportation vehicle at a point in time after zero time. The curve that corresponds with reference numeral 16 is intended to represent a carbon dioxide concentration profile within a confined space within a transportation vehicle derived from an enhanced background carbon dioxide concentration in the vicinity of the confined space within the transportation vehicle such as may be experienced, for example, when operating a transportation vehicle within an enclosed space such as a garage). The curve that corresponds with reference numeral 18 is intended to represent a carbon dioxide concentration profile within a confined space within a transportation vehicle derived from a lower level ambient background carbon dioxide concentration in the vicinity of the confined space within the transportation vehicle. Within the preferred embodiment of the present invention, it is intended to discriminate between the various sources of carbon dioxide, as illustrated within the plot of FIG. 2, which may provide a concentration of carbon dioxide within a confined space within a transportation vehicle.

Figure 3:
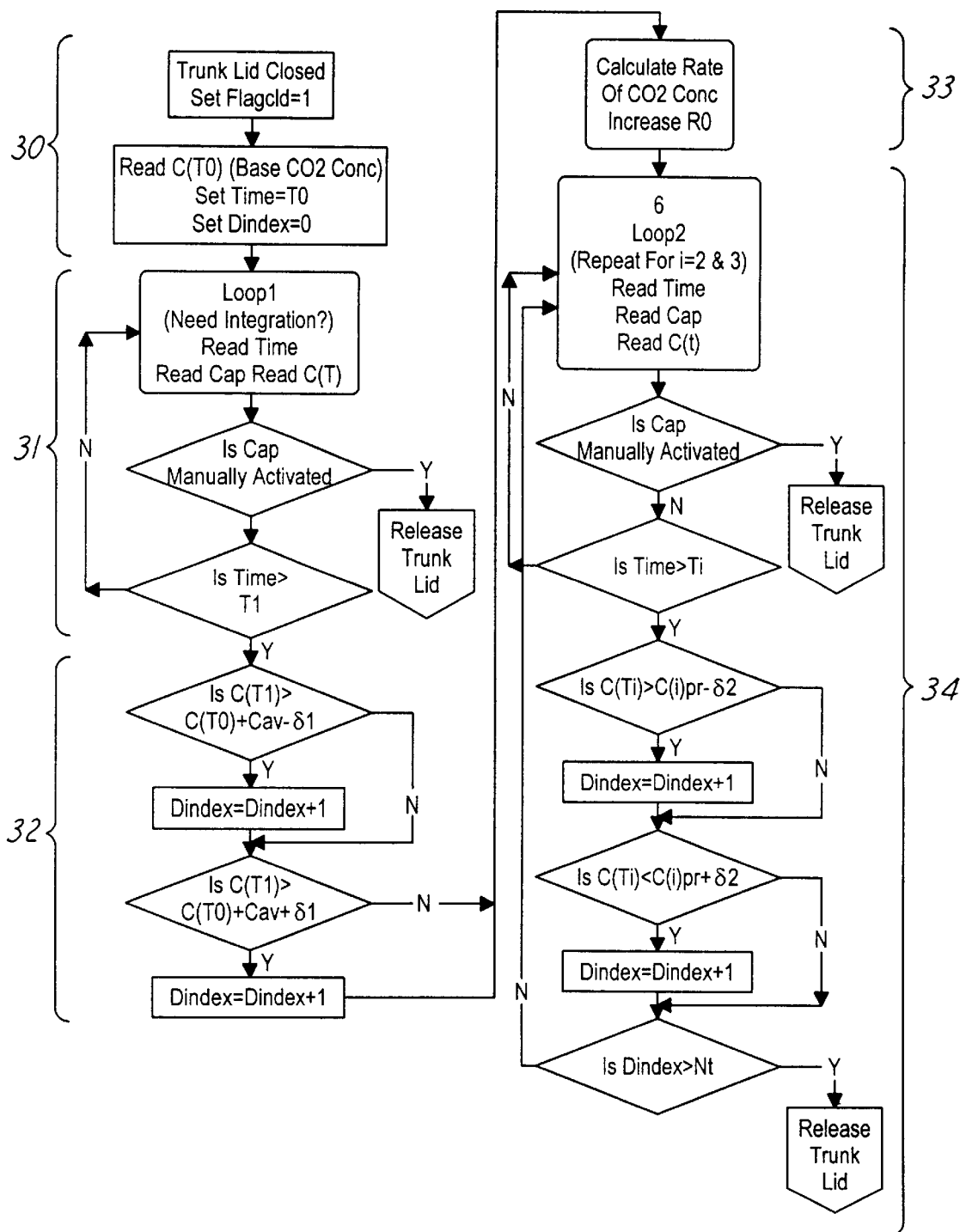
FIG. 3 shows an algorithmic flow diagram for an algorithm programmed into a computing means for detecting a confined occupant within a confined trunk space within a transportation vehicle predicated upon a carbon dioxide concentration within the confined trunk space within the transportation vehicle.

Referring now to FIG. 3, there is shown an algorithmic flow diagram which describes an algorithm. that may be employed in conjunction with the preferred embodiment of the present invention for: (1) determining the presence of a confined occupant within a confined space within a transportation vehicle; and (2) incident to such determination opening the confined space within the transportation vehicle. Although the algorithmic flow diagram of FIG. 3 is directed more specifically towards a confined occupant within confined trunk space within a passenger transportation vehicle, as noted above, the present invention may also be employed for detecting confined occupants within confined spaces within various other types of transportation vehicles.

Referring more specifically to the algorithmic steps that correspond with reference numeral 30 within the algorithmic flow diagram of FIG. 3, the algorithm starts upon closing a trunk lid of a transportation vehicle, which defines a starting time $T_0$ at which is measured a base carbon dioxide concentration $C_0$ within the confined trunk space of the transportation vehicle. Similarly, the algorithm also simultaneously establishes an initial value of an index parameter Dindex of zero at the starting time T0. Within the algorithm as outlined within FIG. 3, Dindex is simply an integrally incremented index parameter that is employed for algorithmic decision making purposes. Similarly, within the present invention and the preferred embodiment of the present invention, the base carbon dioxide concentration $CO_2$ is determined employing a minimum of one carbon dioxide sensor positioned with the confined trunk space within the transportation vehicle. Finally, the algorithm as illustrated in FIG. 3 is programmed within a computing means that is connected to the minimum of the one carbon dioxide sensor and further connected in a fashion such that it may effect opening of the trunk lid. The computing means may include, but is not limited to a computer (in general) or a processor (more specifically), wherein the algorithm may be programmed within the computing means while further employing programming means including but not limited to pre-programmed hardware programming means (i.e., read only memory means) and software programming means.

Referring more particularly to the algorithmic process steps that correspond with reference numeral 31 within the algorithmic flow diagram of FIG. 3, the algorithm then executes a series of repetitive sub-loops within a first loop, wherein there is determined within the confined space within the transportation vehicle a carbon dioxide concentration as a function of time (i.e., a rate of carbon dioxide concentration increase), for each of the series of repetitive sub-loops within the first loop. The first loop then ends at a first preset time interval T1. There is also determined for each of the series of repetitive sub-loops whether there has been manually activated a request Cap for release of the trunk lid. Upon such manual activation of such a request Cap, the trunk lid is released and the algorithm is terminated.

Referring more particularly to the algorithmic process steps that correspond with reference numeral 32 within the algorithmic flow diagram of FIG. 3, upon reaching the first preset time interval T1 there is determined whether the carbon dioxide concentration at the first preset time interval C(T1) is within a first deviation $\delta 1$ of a predetermined average carbon dioxide concentration Cav increase over the base carbon dioxide concentration C(T0) expected at the first preset time interval T1. Based upon a determination of whether the carbon dioxide concentration at the first preset time interval C(T1) is within either or both a positive value of the first deviation $\delta 1$ and a negative value of the first deviation $\delta 1$, the index parameter Dindex is incremented by either 1 or 2.

Within the preferred embodiment of the algorithm as illustrated within the algorithmic flow diagram of FIG. 3, the carbon dioxide concentration at the first preset time interval C(T1), and in particular the first deviation $\delta 1$, are set sufficiently broad as a first approximation such as to include a broad range of potential confined occupants within the confined trunk space within the transportation vehicle.

Referring more specifically to the algorithmic step that corresponds with reference numeral 33 within the algorithmic flow diagram of FIG. 3, the algorithm then calculates a rate of carbon dioxide concentration rise R0 within the enclosed space within the transportation vehicle based upon the first preset time interval T1, the base carbon dioxide concentration C(T0) and the carbon dioxide concentration at the first preset time interval C(T1). This calculated rate of carbon dioxide concentration rise R0 within the enclosed space within the transportation vehicle is then employed within further calculations within the algorithm.

Referring more specifically to the algorithmic steps that correspond with reference numeral 34 within the algorithmic flow diagram of FIG. 3, there is then repetitively determined and appropriately indexed, for a series of at least two additional subsequent loops (and analogously with the algorithmic steps which correspond with reference numeral 31 and reference numeral 32), two additional series of carbon dioxide measurements as a function of time. Within the two additional series of carbon dioxide measurements as a function of time, and as is illustrated within the algorithmic flow diagram of FIG. 3, further indexing of the index parameter Dindex is predicated upon determination of whether a carbon dioxide concentration at a subsequent preset time interval C(T1) is within a second deviation $\delta 2$ of a projected carbon dioxide concentration at the subsequent preset time interval C(i)pr, where the projected carbon dioxide concentration at the subsequent preset time interval C(i)pr is derived from the calculated rate of carbon dioxide increase R0. By employing for determining a projected carbon dioxide concentration at the subsequent time interval C(i)pr the calculated rate of carbon dioxide increase R0 rather than an arbitrary pre-determined average carbon dioxide concentration value Cav, a magnitude of the second deviation $\delta 2$ may be limited and narrowed such as to provide for an enhanced selectivity of the algorithm with respect to discriminating the various sources of carbon dioxide within the enclosed trunk space as illustrated within the plot of FIG. 2. As is finally illustrated in conjunction with the algorithmic steps which correspond with reference numeral 34, the algorithm determines whether the index parameter Dindex has exceeded a predetermined index parameter value Nt and under such circumstances the trunk lid is released. If the index parameter Dindex has not exceeded the predetermined index parameter value Nt, the algorithm may continue subsequent iterative loops. Preferably, the algorithm operates over a time interval of at least about 10 minutes, and more preferably from about 15 to about 30 minutes, which includes at least the first loop and two subsequent loops.

As is understood by a person skilled in the art, the preferred embodiment of the present invention is illustrative of the present invention rather than limiting of the present invention. Revisions and modifications may be made to apparatus, transportation vehicles and methods as disclosed within the context of the preferred embodiment of the present invention, while still providing an apparatus, a transportation vehicle or a method in accord with the present invention, further in accord with the accompanying claims.

What is claimed is:

1. A confined occupant detection apparatus comprising:
    a minimum of one carbon dioxide sensor; and
    a computing means having programmed therein an algorithm appropriate for detecting an occupant within a confined space in a vehicle based upon an analysis of a carbon dioxide concentration measured within the confined space in the vehicle while employing the minimum of one carbon dioxide sensor.

2. The confined occupant detection apparatus of claim 1 further comprising a means for opening the confined space in the vehicle based upon detecting the occupant within the confined space in the vehicle while employing the computing means having programmed therein the algorithm, the means for opening the confined space being effected by the computing means.

3. The confined occupant detection apparatus of claim 1 wherein the confined space is selected from the group consisting of a confined trunk space within a passenger vehicle and a confined cargo space within a vehicle other than a passenger vehicle.

4. The confined occupant detection apparatus of claim 1 wherein the algorithm analyzes the carbon dioxide concentration within the confined space for a time period of at least about 10 minutes.

5. The confined occupant detection apparatus of claim 1 wherein the confined occupant is selected from the group consisting of an adult, a juvenile, an infant and a carbon dioxide respiring animal.

6. A transportation vehicle having incorporated therein a confined occupant detection apparatus comprising:
   a vehicle body;
   a minimum of one carbon dioxide sensor assembled into a confined space within the vehicle body; and
   a computing means having programmed therein an algorithm appropriate for detecting an occupant within the confined space in the vehicle body based upon an analysis of a carbon dioxide concentration measured within the confined space while employing the minimum of one carbon dioxide sensor.

7. The transportation vehicle of claim 6 further comprising a means for opening the confined space in the vehicle based upon detecting the occupant within the confined space while employing the computing means having programmed therein the algorithm, the means for opening the confined space being effected by the computing means.

8. The transportation vehicle of claim 6 wherein the transportation vehicle is selected from the group consisting of passenger vehicles, sport utility vehicles, light utility vehicles and heavy utility vehicles.

9. The transportation vehicle of claim 6 wherein the confined space is selected from the group consisting of a confined trunk space in a passenger vehicle and a confined cargo space in a vehicle other than a passenger vehicle.

10. The transportation vehicle of claim 6 wherein the algorithm analyzes the carbon dioxide concentration within the confined space for a time period of at least about 10 minutes.

11. The transportation vehicle of claim 6 wherein the confined occupant is selected from the group consisting of an adult, a juvenile, an infant and a carbon dioxide respiring animal.

12. A method for detecting a confined occupant within a transportation vehicle comprising:
   providing a vehicle, the vehicle having assembled therein a confined occupant detection apparatus comprising:
      a minimum of one carbon dioxide sensor assembled within a confined space in the vehicle; and
      a computing means having programmed therein an algorithm appropriate for detecting a confined occupant within the confined space in the vehicle based upon a carbon dioxide concentration within the confined space as measured while employing the minimum of one carbon dioxide sensor; and
   activating the confined occupant detection apparatus to detect a confined occupant within the confined space in the vehicle.

13. The method of claim 12 further comprising providing a means for opening the confined space in the vehicle based upon detecting the occupant within the confined space while employing the computing means having programmed therein the algorithm, the means for opening the confined space being effected by the computing means.

14. The method of claim 12 wherein the transportation vehicle is selected from the group consisting of passenger vehicles, sport utility vehicles, light utility vehicles and heavy utility vehicles.

15. The method of claim 12 wherein the confined space is selected from the group consisting of a confined trunk space within a passenger vehicle and a confined cargo space in a vehicle other than a passenger vehicle.

16. The method of claim 12 wherein the algorithm analyzes the carbon dioxide concentration within the confined space for a time period of at least about 10 minutes.

17. The method of claim 12 wherein the confined occupant is selected from the group consisting of an adult, a juvenile, an infant and a carbon dioxide respiring animal.

* * * * *